US010265314B2

(12) United States Patent
Sandner et al.

(10) Patent No.: US 10,265,314 B2
(45) Date of Patent: Apr. 23, 2019

(54) SGC STIMULATORS IN COMBINATION WITH ADDITIONAL TREATMENT FOR THE THERAPY OF CYSTIC FIBROSIS

(71) Applicant: BAYER PHARMA AKTIENGESELLSCHAFT, Berlin (DE)

(72) Inventors: Peter Sandner, Wuppertal (DE); Johannes-Peter Stasch, Solingen (DE); Michael Hahn, Langenfeld (DE); Markus Follmann, Köln (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 88 days.

(21) Appl. No.: 14/906,305

(22) PCT Filed: Jul. 21, 2014

(86) PCT No.: PCT/EP2014/065607
§ 371 (c)(1),
(2) Date: Jan. 20, 2016

(87) PCT Pub. No.: WO2015/011086
PCT Pub. Date: Jan. 29, 2015

(65) Prior Publication Data
US 2016/0158233 A1    Jun. 9, 2016

(30) Foreign Application Priority Data
Jul. 25, 2013  (EP) .................................... 13177992

(51) Int. Cl.
A61K 31/47      (2006.01)
A61K 31/53      (2006.01)
A61P 11/00      (2006.01)
A61K 31/197     (2006.01)
A61K 31/404     (2006.01)
A61K 31/425     (2006.01)
A61K 31/427     (2006.01)
A61K 31/443     (2006.01)
A61K 31/506     (2006.01)
A61K 31/519     (2006.01)
A61K 31/4439    (2006.01)
A61K 31/5377    (2006.01)

(52) U.S. Cl.
CPC .......... A61K 31/506 (2013.01); A61K 31/197 (2013.01); A61K 31/404 (2013.01); A61K 31/425 (2013.01); A61K 31/427 (2013.01); A61K 31/443 (2013.01); A61K 31/4439 (2013.01); A61K 31/47 (2013.01); A61K 31/519 (2013.01); A61K 31/53 (2013.01); A61K 31/5377 (2013.01); A61P 11/00 (2018.01)

(58) Field of Classification Search
CPC .. A61K 31/506; A61K 31/197; A61K 31/404; A61K 31/425; A61P 11/00
USPC ........................................................ 514/243
See application file for complete search history.

(56) References Cited

U.S. PATENT DOCUMENTS

| | | |
|---|---|---|
| 6,180,565 B1 | 1/2001 | Fürstner et al. |
| 6,180,656 B1 | 1/2001 | Fürstner et al. |
| 6,335,334 B1 | 1/2002 | Schindler et al. |
| 6,693,102 B2 | 2/2004 | Stasch et al. |
| 6,743,798 B1 | 6/2004 | Straub et al. |
| 6,833,364 B1 | 12/2004 | Straub et al. |
| 6,864,287 B1 | 3/2005 | Alonso-Alija et al. |
| 7,087,644 B1 | 8/2006 | Alonso-Alija et al. |
| 7,173,037 B2 | 2/2007 | Alonso-Alija et al. |
| 7,674,825 B2 | 3/2010 | Alonso-Alija et al. |
| 7,705,043 B2 | 4/2010 | Alonso-Alija et al. |
| 2002/0183365 A1 | 12/2002 | Wagle et al. |
| 2004/0087591 A1 | 5/2004 | Garvey et al. |
| 2004/0176446 A1 | 9/2004 | Alonso-Alija et al. |
| 2006/0052397 A1 | 3/2006 | Alonso-Alija et al. |
| 2006/0094769 A1 | 5/2006 | Alonso-Alija et al. |
| 2008/0081816 A1 | 4/2008 | Chen et al. |
| 2009/0209556 A1 | 8/2009 | Bittner et al. |
| 2009/0215769 A1 | 8/2009 | Krahn et al. |
| 2009/0221570 A1 | 9/2009 | Haning et al. |
| 2009/0286781 A1 | 11/2009 | Krahn et al. |
| 2010/0210643 A1 | 8/2010 | Sandner et al. |
| 2011/0028493 A1 | 2/2011 | Matsuuaga et al. |
| 2012/0022028 A1 | 1/2012 | Sandner et al. |
| 2013/0035340 A1 | 2/2013 | Sandner et al. |
| 2013/0053393 A1 | 2/2013 | Frangakis et al. |
| 2013/0158028 A1 | 6/2013 | Stasch et al. |
| 2014/0038956 A1 | 2/2014 | Hirth-Dietrich et al. |

FOREIGN PATENT DOCUMENTS

| WO | WO 00/02851 A1 | 1/2000 |
|---|---|---|
| WO | WO 00/06568 A1 | 2/2000 |

(Continued)

OTHER PUBLICATIONS

Taylor et al., "Hypertonic Saline Treatment of Cystic Fibrosis", The Annals of Pharmacotherapy, vol. 41, No. 3, pp. 481-484 (Mar. 2007).*

(Continued)

Primary Examiner — Kevin E Weddington
(74) Attorney, Agent, or Firm — Ice Miller LLP

(57) ABSTRACT

The present invention relates to soluble guanylate cyclase (sGC) and to phosphodiesterases (PDEs) and the pharmacology of sGC stimulators, sGC activators and PDE inhibitors (PDE5i) in combination with a) treatments, leading to increased cGMP mobilization, and/or b) tretaments correcting and/or potentiatiating CFTR function, and/or c) treatments currently used as standard of care in Cystic Fibrosis, and/or d) antinflammatory treatments for the preparation of medicaments for the treatment of Cystic Fibrosis (CF) with improved efficacy over methods of treatments already known.

8 Claims, No Drawings

(56) References Cited

FOREIGN PATENT DOCUMENTS

| | | |
|---|---|---|
| WO | 01/19355 A2 | 3/2001 |
| WO | WO 01/19780 A2 | 3/2001 |
| WO | WO 03/095451 A1 | 11/2003 |
| WO | WO 2009/003249 A1 | 1/2009 |
| WO | WO 2009/068652 A1 | 6/2009 |
| WO | WO 2009/071504 A1 | 6/2009 |
| WO | WO 2009/123316 A1 | 10/2009 |
| WO | 2009/149278 A1 | 12/2009 |
| WO | 2010/065275 A1 | 6/2010 |
| WO | WO 2011/095534 A1 | 8/2011 |
| WO | WO 2011095534 A1 * 8/2011 ............ A61K 31/18 |
| WO | WO 2011/147809 A1 | 12/2011 |
| WO | WO 2012/139888 A1 | 10/2012 |

OTHER PUBLICATIONS

Agonist-Merriam Webster Medline Plus Online Medical Dictionary, http://www.merriam-webster.com/medlineplus/agonist, (2 pages).
Bischoff et al., "Bay 41-2272: A Stimulator of Soluble Guanylyl Cyclase Induces Nitric Oxide-Dependent Penile Erection in Vivo," Urology, (2003), vol. 61, No. 2, pp. 464-467.
Chen et al., "Mechanisms of Cystic Fibrosis Transmembrane Conductance Regulator Activation by S-Nitrosoglutathione," The Journal of Biological Chemistry, (Apr. 7, 2006), vol. 281, No. 14, pp. 9190-9199.
Levitra Product Information—Bayer Pharmaceuticals Corporation 2007, (30 pages).
Mittendorf et al., Discovery of Riociguat (BAY 63-2521): A Potent, Oral Stimulator of Soluble Guanylate Cyclase for the Treatment of Pulmnary Hypertension, Chem Med Chem, (2009), vol. 4, pp. 853-865.
Nagayama et al., "Sustained Soluble Guanylate Cyclase Stimulation Offsets Nitric-Oxide Synthase Inhibition to Restore Acute Cardiac Modulation by Sildenafil," The Journal of Pharmacology and Experimental Therapeutics, (2008), vol. 326, No. 2, pp. 380-387.
Poschet et al., "Endosomal Hyperacidification in Cystic Fibrosis is due to Defective Nitric Oxide-Cylic GMP Signalling Cascade," EMBO Reports, (2006), vol. 7, No. 5, pp. 553-559.
Poschet et al. "Pharmacological Modulation of cGMP Levels by Phosphodiesterase 5 Inhibitors as a Therapeutic Strategy for Treatment of Respiratory Pathology in Cystic Fibrosis," American Journal of Physiology—Lung Cellular and Molecular Physiology, (2007), vol. 293, pp. L712-L719.
Rodgers et al., "Pharmacological Treatment of the Biochemical Defect in Cystic Fibrosis Airways," European Respiratory Journal, (2001), vol. 17, pp. 1314-1321.
Stasch et al., "NO- and Haem-Independent Activation of Soluble Guanylyl Cyclase: Molecular Basis and Cardiovascular Implications of a New Pharmacological Principle," British Journal of Pharmacology, (2002), vol. 136, No. 5, pp. 773-781.
Van Goor et al., "Rescue of CF Airway Epithelial Cell Function in Vitro by a CFTR Potentiator, VX-770," PNAS, Nov. 3, 2009), vol. 106, No. 44, pp. 18825-18830.
International Search Report (PCT/ISA/210) dated Sep. 22, 2014, by the European Patent Office as the International Searching Authority for International Application No. PCT/EP2014/065607.
Written Opinion (PCT/ISA/237) dated Sep. 22, 2014, by the European Patent Office as the International Searching Authority for International Application No. PCT/EP2014/065607.

Bob Lubamba et al., "Preclinical Evidence that Sildenafil and Vardenafil Activate Chloride Transport in Cystic Fibrosis", American Journal of Respiratory and Critical Care Medicine, vol. 177, No. 5, Mar. 1, 2008, pp. 506-515, XP002630669.
Kavisha Arora et al., "Stabilizing rescued delF508 CFTR at the plasma membrane by potentiation of its interaction with Nz+/H+ exchanger regulatory factor 1", The FASEB Journal, Joint Annual Meeting of the ASPET/BPS at Experimental Biology (EB), vol. 27, No. 4, Suppl. 1, Apr. 1, 2013, p. 553, XP008171907.
Frederic Becq, "Cystic Fibrosis Transmembrane Conductance Regulator Modulators for Personalized Drug Treatment of Cystic Fibrosis", Drugs, vol. 70, No. 3, Jan. 1, 2010, pp. 241-259, XP008171892.
"Study of VX-661 Alone and in Combination with VX-770 in Subjects Homozygous to the F508del-CFTR Mutation", Retrieved from the Internet: URL:http://clinicaltrials.gov/archive/NCT01531673/2013_07_08, Jul. 18, 2013, the whole document, XP002729415.
Graeme W. Carlile et al., Correctors of Protein Trafficking Defects Identified by a Novel High-Throughput Screening Assay, Chem Bio Chem, 2007, 8, pp. 1012-1020.
LL Clarke, "Phosphodiesterase 5 Inhibitors and Cystic Fibrosis", American Journal Respiratory and Critical Care Medicine, 2008, vol. 177, pp. 469-470.
Bryan R. Cobb et al., "Adenosine Receptors and Phosphodiesterase Inhibitors Stimulate Cl-Secretion in Calu-3 Cells", American Journal Respiratory and Molecular Biology, 2003, vol. 29, pp. 410-418.
RL Dormer et al., "Sildenafil (Viagra) corrects AF508-CFTR location in nasal epithelia cells from patients with cystic fibrosis", Thorax, Aug. 15, 2004, vol. 60, pp. 55-59, XP008125970.
Karoline Droebner et al., "Modification of the salivary secretion assay in F508del mice—The murine equivalent of the human sweat test", J Cyst Fibros, 2013, vol. 12, pp. 630-637.
K. Droebner et al., "Modification of the salivary secretion assay in F508del mice—Salivary chloride quantification and its correlation to the human sweat test", Cell Biology/Cell Physiology/CFTR, 2014, p. S60, 50.
Oleg V. Evgenov et al., "NO-independent stimulators and activators of soluble guanylate cyclase: discovery and therapeutic potential", Nat Rev Drug Discov, 2006, vol. 5, No. 9, pp. 755-768.
Margaret A. McPherson et al., "A cyclic nucleotide PDE5 inhibitor corrects defective mucin secretion in submandibular cells containing antibody directed against the cystic fibrosis transmembrane conductance regulator protein", FEBS Letters, 1999, vol. 464, pp. 48-52.
Renaud Robert et al., "Structural analog of sildenafil identified as a novel corrector of the F508del-CFTR trafficking defect", Mol Pharmacol, 2008, vol. 73, pp. 478-489.
P. Sandner et al., "PDE5 inhibitors beyond erectile dysfunction", Int J Impot Res, 2007, vol. 19, No. 6, pp. 533-543.
Harald H.H.W.Schmidt et al., "cGMP: Generators, Effectors and therapeutic implications", Handbook of Experimental Pharmacology, 2007, vol. 191, the whole book.
Johannes-Peter Stasch et al., "NO-independent regulatory site on soluble guanylate cyclase", Nature, 2001, vol. 8, pp. 212-215.
Sandner et al., "Erectile Dysfucntion and Lower Urinary Tract," Handbook Exper. Pharmacol. 2009, vol. 191:507-531.
International Search Report (Form PCT/ISA/210) and Written Opinion of the International Searching Authority (Form PCT/ISA/237) dated Apr. 12, 2011, by the Europen Patent Office in the International Application No. PCT/EP2011/051532 (12 pages).

* cited by examiner

SGC STIMULATORS IN COMBINATION WITH ADDITIONAL TREATMENT FOR THE THERAPY OF CYSTIC FIBROSIS

This application is the national stage entry of PCT Application PCT/EP2014/065607, filed on Jul. 21, 2014, which claims priority to EP Application No. 13177992.8 filed on Jul. 25, 2013, the entire contents of each of which applications are hereby incorporated herein by reference in their entireties.

The present invention relates to soluble guanylate cyclase (sGC) and to phosphodiesterases (PDEs) and the pharmacology of sGC stimulators, sGC activators and PDE inhibitors (PDE5i) in combination with a) treatments, leading to increased cGMP mobilization, and/or b) tretaments correcting and/or potentiatiating CFTR function, and/or c) treatments currently used as standard of care in Cystic Fibrosis, and/or d) antinflammatory treatments for the preparation of medicaments for the treatment of Cystic Fibrosis (CF) with improved efficacy over methods of treatments already known.

BACKGROUND OF THE INVENTION

The cyclic nucleotides, cyclic adenosine monophosphate (cAMP) and cyclic guanosine monophosphate (cGMP), were discovered decades ago and represent one of the most important second messenger pathway within cells. It is well established that the regulation of intra-cellular cGMP pools have substantial impact on physiology, and pathophysiology and is one basic principle of pharmacological intervention (Eugenov et al. 2006; Schmidt et al. 2009). Nitrates and PDE5 inhibitors (PDE5i) which could increase intra-cellular cGMP levels are therefore already approved therapies for Angina, and Pulmonary Arterial Hypertension (PAH) or Erectile Dysfunction (ED), respectively. More recently discovered sGC stimulators and activators, are in advanced states of clinical development for PAH and Heart Failure. Therefore, targeting the NO/cGMP pathway by either cGMP production (nitrates, sGC stimulators, sGC activators) or cGMP break-down (PDE5i) became a very effective pharmacological intervention strategy in various diseases.

On a molecular level, NO-production results in stimulation of the soluble guanylate cyclase (sGC) resulting in enhanced cGMP formation. Consecutively, cGMP regulates different downstream targets, mainly cGMP regulated protein kinases (G-Kinases), cGMP-regulated phosphodiesterases (PDEs) and cGMP regulated ion channels which translates the NO-signal and rise in cGMP and in a decrease of intracellular free calcium. Therefore, the most prominent response of increasing intracellular cGMP, especially in the Smooth Muscle Cell (SMC), is relaxation. In addition, antiproliferative, antifibrotic or proapoptotic effects of cGMP are discussed and might expand the treatment options for PDE5 inhibitors (Sandner et al. 2007, Schmidt et al. 2009). More recently some lines of evidence showed that PDE5 inhibitors could also influence chloride secretion via the chloride channel CFTR and might be useful for the treatment of Cystic Fibrosis (Clarke 2008).

Cystic fibrosis (CF) is one of the most prevalent genetic disorders, caused by mutation of a single gene, the CFTR-channel, affecting 1 out of 2500-3000 newborns. In this disease, abnormal ion transport across the respiratory epithelia leads to dehydrated airway surface and viscous and poorly-cleared mucus. This contributes to chronic infections of the airways and high morbidity and early mortality. Up to now, the treatment is mainly focused on anti-infective treatment and lung transplantation but no causal therapy focusing on the correction and potentiation of impaired CFTR function is available.

On the molecular level a mutation in the CFTR gene results in CF. A broad variety of CF-causing mutations in the CFTR gene have been identified. However, the most prevalent mutation is a deletion of the phenylalanine in position 508 of the CFTR amino acid sequence, and is termed as ΔF508-CFTR. This mutation occurs in approximately 70%-80% of the cases of CF and is associated with a severe disease.

The deletion of residue 508 in ΔF508-CFTR prevents the mature protein from correct processing and folding. This missfolded CFTR could not, or not completely, exit the ER, and traffic to the plasma membrane. As a result, the number of channels present in the membrane in CFTR-patients is far less than observed in cells expressing wild-type CFTR. In addition the mutated channel exhibited reduced channel activity. Both, the reduced number of channels in the epithelial membranes and the reduced channel acitivity results in significantly impaired anion transport across epithelia leading to defective ion and fluid transport. This causes an imbalance in lung epithelial fluid transport and finally an excessive accumulation of viscosous mucus in the lungs. Moreover impaiered CFTR-function also influences e.g. pancreatic function, gastro-intestinal functions, liver function, functions of secretory glands or insulin secretion.

In summary, impaired CFTR function by several mutations cause cystic fibrosis. Therefore correction and/or potentiation of CFTR function of these mutations could present a causal treatment option for Cystic Fibrosis (CF).

In addition correction and/or potentiation of CFTR function could present a causal treatment option for pancreatic dysfunction, liver dysfunction, dry mouth, dry eye, Sojegren's syndrome, and CF-induced diabetes.

It was shown, that in lung epithelial cells sildenafil—a potent and selective PDE5i—increased CFTR-driven chloride secretion (Cobb et. al 2003). In addition trafficking and functional activity of mutated CFTR-channels to the cell membrane could be influenced by PDE5i in vitro (Dormer et. al 2005, Carlile et al. 2007, Robert et al. 2008). In line with these findings it was demonstrated that PDE5 inhibitors when used in animal models of Cystic fibrosis (CF) are able to reduce mucin secretin (Mc Pherson 1999) and could influence chloride secretion (Lubamba et al. 2008). Therefore it was hypothesized that PDE5 inhibitors could be used for the treatment of Cystic Fibrosis (Cobb 1999, Lubamba et. al. 2008, Clarke 2008).

However, the use of PDE5 inhibitors is limited since they could only inhibit cGMP degradation. In cases in which NO-dependent cGMP production is low, their efficacy is at least partially impaired. Very interestingly, compounds have been described recently that could overcome this limitation of PDE5 inhibitors via direct stimulation or activation of the sGC. Two classes of compounds have been identified that activate the sGC NO-independently, the heme-dependent sGC stimulators, such as BAY 41-2272 according to compound of the formula (4a), BAY 41-8543 according to compound of the formula (1), BAY 59-3394 according to compound of the formula (2), the compound according to formula (3a), BAY 63-2521 according to compound of the formula (3), and BAY 60-4552 according to compound of the formula (4), and heme-independent sGC activators, such as BAY 58-2667 according to compound of the formula (5), HMR-1766 according to compound of the formula (6), (Stasch et al. 2001, for review see Evgenov et al. 2006), and the sGC activators disclosed in WO 2012/139888, herewith incorporated by reference.

In addition, it has been shown very recently that correction of deltaF508 function, using a corrector compound (VX-809) is not sufficient for a clinically meaningful treatment effect in deltaF508 CF patients (M. Boyle, NACCF-presentation November 2012). However, when VX-809 was combined with a potentiator compound, i.e. VX-770, restoration of deltaF508 function was significantly improved, resulting in a clinical benefit for the CF-patient.

sGC stimulators, sGC activators and/or PDE5 inhbitors in combination with other pharmacological compounds which lead to increased cGMP mobilization, i.e. Nitrates, NO-Donors, Natriumnitroprussid, Nitroglycerine, Isosorbidmononitrate, Isosorbiddinitrate, Molsidomin or SIN-1, inhaled Nitric Oxide (NO), could result in superior clinical benefits for CF patients.

In addition, sGC stimulators, sGC activators and/or PDE5 inhbitors in combination with other molecules, correcting and potentiating i.e. deltaF508 CFTR function, i.e. VX-809, VX-770, VX-661 could significantly enhance the effect of sGC stimulators, sGC activators and PDE5 inhbitors, resulting in superior clinical benefits for CF patients.

In addition, combination of of sGC stimulators, sGC activators and/or PDE5 inhbitors with the current standard of care in CF, i.e. systemic or nebulized antibiotics, Dornase Alpha (rhDNase), hypertonic saline, asthma treatments, could result in superior clinical benefits for CF patients. In addition, combination of of sGC stimulators, sGC activators and/or PDE5 inhbitors with anti-inflammatory drugs, i.e. systemic or nebulized glucocorticoids, serine protease inhibitors, elastase inhibitors, could result in superior clinical benefits for CF patients.

We therefore investigated sGC stimulators and sGC activators, i.e. BAY 41-2272, BAY 60-4552 according to compound of the formula (4a, 4), alone or in combinations with PDE5 inhibitors, i.e. vardenafil, in vivo, in CFTR-transgenic animal models, i.e. in deltaF508 CFTR mice. We compared these effects with correctors (i.e.) VX-809 and potentiators (VX-770). In addition, effective concentrations and dosages of the aforementioned compounds were combined and efficacy in murine CF-models was investigated.

In particular, PDE5 inhibitors, sGC stimulators, sGC activators, potentiators (i.e. VX-770), correctors (i.e. VX-809) alone or combinations thereof, were tested:
  in transgenic mice expressing the delta F508CFTR channel, on nasal potential difference, on salivation secretion as on salivation chloride content as descriebed recently (Droebner and Sandner; 2013).
  in transgenic mice not expressing the CFTR, on nasal potential difference, on salivation secretion as on salivation chloride content. as descriebed recently (Droebner and Sandner; 2013).

We could demonstrate that stimulators and activators of the soluble guanylate cyclase, corrected and potentiated CFTR function, presenting a new causal treatment option for CF-patients. In addition, we found that combinations of sGC stimulators or sGC activators with PDE5i showed more than additive effects on correction and potentiation. Effects of sGC stimulators, sGC activators and/or PDE5 inhibitors alone or in combination were superior to the effects seen by correctors, i.e. VX-809. Combination of sGC stimulators or sGC activators and PDE5 inhibitors with correctors, i.e. VX-809 showed completely unexpected overadditive effects.

In summary we discovered that combinations of sGC stimulators or sGC activators and/or PDE5 inhibitors when combined with other treatment options could correct and potentiale CFTR function in vivo in an overadditive mode. Due to this increased efficacy combinations of sGC stimulators, sGC activators and/or PDE5 inhibitors, with correctors having a different mode of action could become a highly effective treatment of Cystic Fibrosis (CF).

DISCLOSURE OF THE INVENTION

Pulmonary disorders, addressed by therapeutic agents of the invention which in particular and with substantial advantage can be treated by the above mentioned sGC stimulators or sGC activators alone, or in combination with PDE5 inhibitors, are lung diseases, comprising Cystic Fibrosis (CF)

Secretory disorders, addressed by therapeutic agents of the invention which in particular and with substantial advantage can be treated by the above mentioned sGC stimulators or sGC activators alone, or in combination with PDE5 inhibitors, comprising but not limited to pancretetic dysfunction, gastrointestinal dysfunction, liver diseases, and cystic-fibrosis related diabetes mellitus (CFRD).

Other diseases, addressed by therapeutic agents of the invention which in particular and with substantial advantage can be treated by the above mentioned sGC stimulators or sGC activators alone, or in combination with PDE5 inhibitors, including, but not limited to, chronic obstructive pulmonary disease (COPD), dry eye disease, dry mouth diseases, and Sjoegren's Syndrome.

All diseases, addressed by therapeutic agents of the invention which in particular and with substantial advantage can be treated by the above mentioned sGC stimulators or sGC activators alone, or in combination with PDE5 inhibitors, are disease in which altered chloride secretion via CFTR is causally involved.

The invention provides sGC stimulators or sGC activators alone, or in combination whith PDE5 inhibitors which are useful for the treatment of Cystic Fibrosis (CF), and superior in efficacy over methods of treatment already known.

The invention provides sGC stimulators or sGC activators alone, or in combination whith PDE5 inhibitors which are useful for the treatment of Cystic Fibrosis (CF), and superior in the side effect profile over methods of treatment already known.

An embodiment of the invention are sGC stimulators, sGC activators and/or PDE5 inhibitors in combination with other pharmacological compounds which lead to increased cGMP mobilization, i.e. Nitrates, NO-Donors, Natriumnitroprussid, Nitroglycerine, Isosorbidmononitrate, Isosorbiddinitrate, Molsidomin or SIN-1, inhaled Nitric Oxide, which are useful for the treatment of Cystic Fibrosis (CF), and superior in efficacy over methods of treatment already known.

Another embodiment of the invention are sGC stimulators, sGC activators and/or PDE5 inhibitors in combination with compounds correcting and potentiating i.e. deltaF508 CFTR function, i.e. VX-809, VX-770, VX-661 which are useful for the treatment of Cystic Fibrosis (CF), and superior in efficacy over methods of treatment already known.

Another embodiment of the invention are sGC stimulators, sGC activators and/or PDE5 inhibitors in combination with the current standard of care in CF, i.e. systemic or nebulized antibiotics, Dornase Alpha (rhDNase), hypertonic saline, asthma treatments, which are useful for the treatment of Cystic Fibrosis (CF), and superior in efficacy over methods of treatment already known.

Another embodiment of the invention are sGC stimulators, or sGC activators and/or PDE5 inhibitors in combination with anti-inflammatory drugs, i.e. systemic or nebulized glucocorticoids, serine protease inhibitors, elastase inhibitors which are useful for the treatment of Cystic Fibrosis (CF), and superior in efficacy over methods of treatment already known.

A Guanylate cyclase (sGC) stimulator and sGC activator is preferably a compound selected from the group comprising 2-[1-(2-fluorobenzyl)-1H-pyrazolo[3,4-b]pyridine-3-yl]-5-(4-morpholinyl)-4,6-pyrimidinediamine (1), described also as example 16 in WO 00/06569, herein incorporated by reference, 2-[1-(2-fluorobenzyl)-1H-pyrazolo[3,4-b]pyridine-3-yl]-5-(4-pyridinyl)-4-pyrimidine-amine (2), described also as example 1 in WO 02/42301, herein incorporated by reference, methyl-4,6-diamino-2-[1-(2-fluorobenzyl)-1H-pyrazolo[3,4-b]pyridine-3-yl]-5-pyrimidinyl(methyl)carbamate (3), described also as example 8 in WO 03/095451, herein incorporated by reference, methyl-{4,6-diamino-2-[5-fluor-1-(2-fluorbenzyl)-1H-pyrazolo[3,4-b]pyridine-3-yl]pyrimidine-5-yl}carbamate (3a), described also as example 1 in WO 2011/147809, herein incorporated by reference methyl-4,6-diamino-2-[1-(2-fluorobenzyl)-1H-pyrazolo[3,4-b]pyridin-3-yl]-5-pyrimidinylcarbamate (4), described also as example 5 in WO 03/095451, herein incorporated by reference, 3-(4-amino-5-cyclopropylpyrimidine-2-yl)-1-(2-fluorbenzyl)1H-pyrazolo[3,4-b]pyridine (4a), described also as example 1 in WO 00/06568, herein incorporated by reference, and 4-({(4-carboxybutyl)[2-(2-{[4-(2-phenylethyl)benzyl]oxy}phenyl)ethyl]amino}methyl)benzoic acid (5), described also as example 8a in WO 01/019780, herin incorporated by reference, 5-chloro-2-(5-chlorothiophene-2-sulfonylamino-N-(4-(morpholine-4-sulfonyl)-phenyl)-benzamide sodium salt (6), described in WO00/02851, 2-(4-chloro-phenylsulfonylamino)-4,5-dimethoxy-N-(4-(thiomorpholine-4-sulfonyl)-phenyl)-benzamide (7), described in WO00/02851, 1-{6-[5-chloro-2-({4-trans-4-}trifluoromethyl)cyclohexyl]benzyl}oxy)phenyl]pyridin-2-yl}-5-(trifluoromethyl)-1H-pyrazole-4-carboxylic acid (8), described in WO 2009/032249, 1-[6-(2-(2-methyl-4-(4-trifluoromethoxyphenyl)benzyloxy)-phenyl)pyridine-2-yl]-5-trifluoromethyl-pyrazole-4-carboxylic acid (9), described in WO 2009/071504, 1[6-(3,4-dichlorophenyl)-2-pyridinyl-5-(trifluoromethyl)-1H-pyrazole-4-caboxylic acid (10), described in WO 2009/068652, 1-({2-[3-chloro-5-(trifluoromethyl)phenyl]-5-methyl-1,3-thiazol-4-yl}methyl)-1H-pyrazole-4-carboxylic acid (11), 4-({2-[3-(trifluoromethyl)phenyl]-1,3-thiazol-4-yl}methyl)benzoic acid (12) and 1-({2-[2-fluoro-3-(trifluoromethyl)phenyl]-5-methyl-1,3-thiazol-4-yl}methyl)-1H-pyrazole-4-carboxylic acid (13) described in WO 2009/123316 sGC activators disclosed in WO 2012/139888, herewith incorporated by reference.

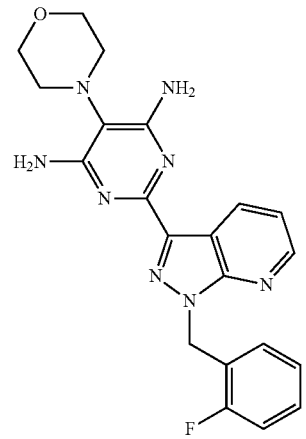

(1)

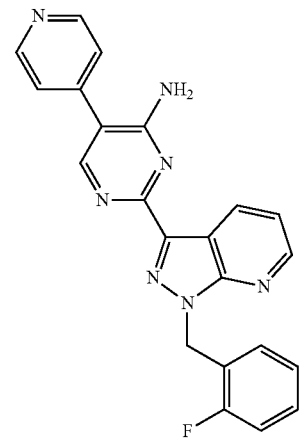

(2)

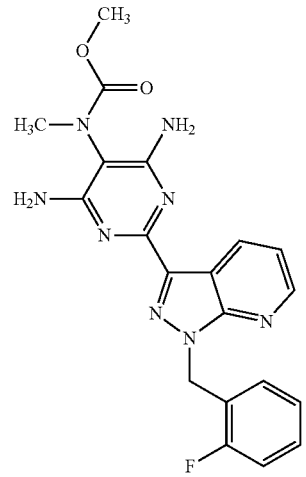

(3)

(4)
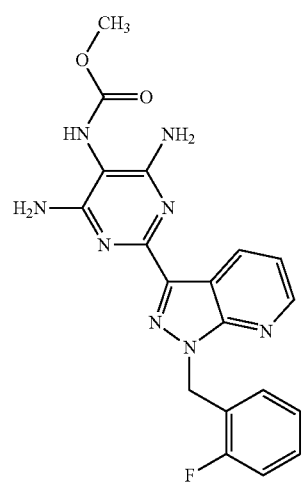
(3a)
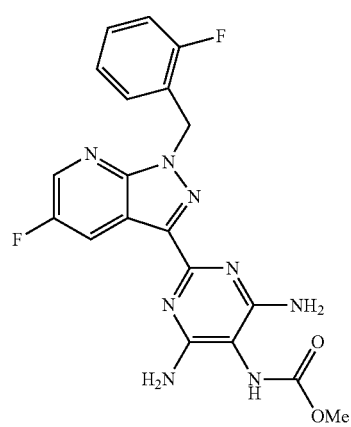
(4a)
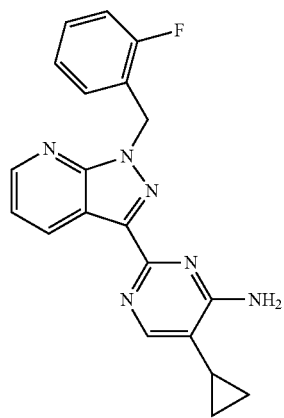
(5)
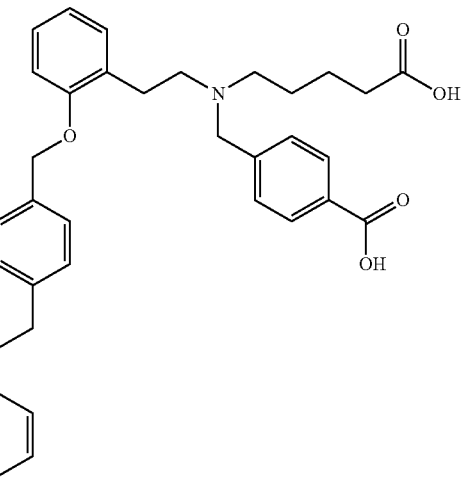
(6)
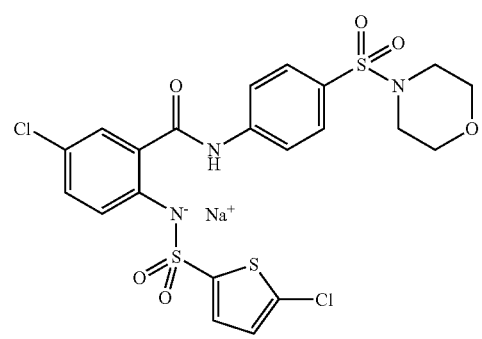
(7)
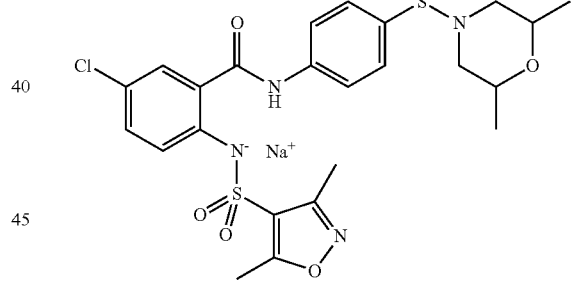
(8)
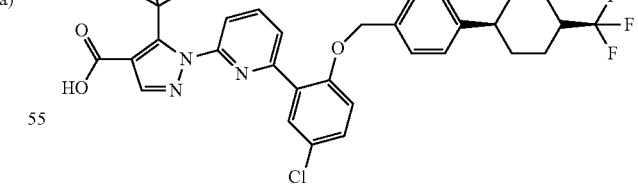
(9)
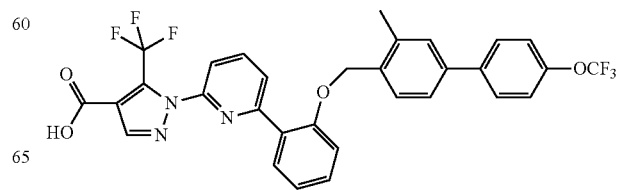

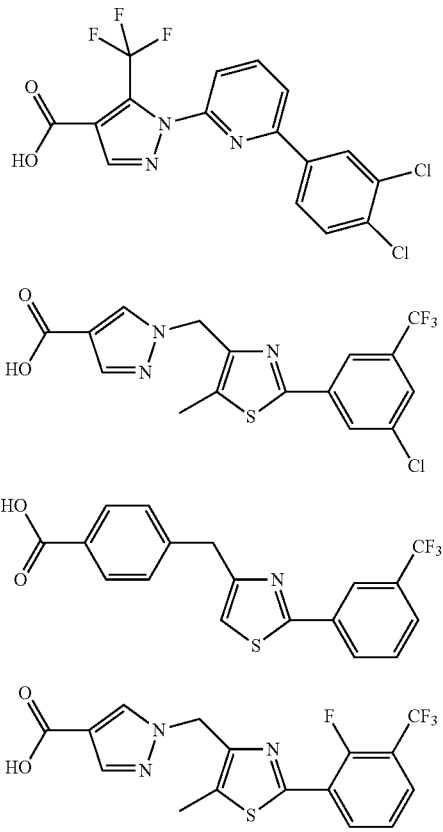

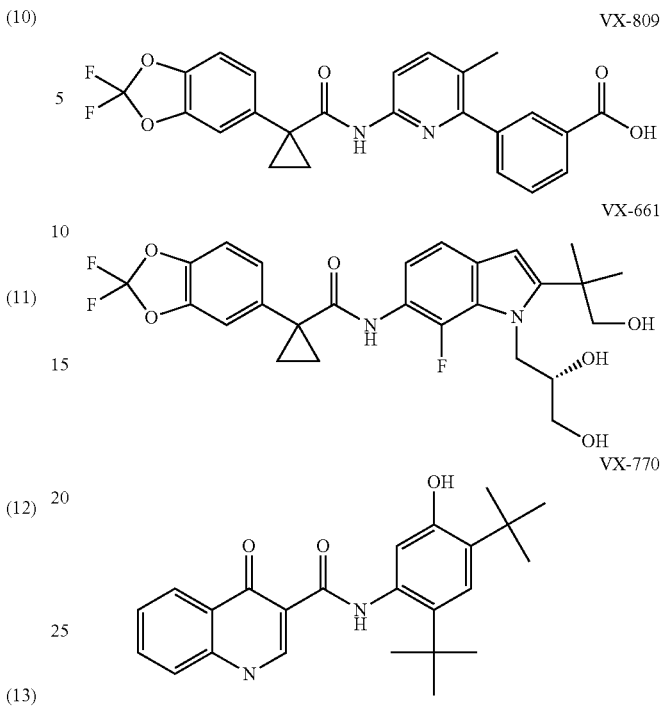

Compounds (1), (2), (3), (3a), (4) and (4a) are known soluble guanylate cyclase (sGC) stimulators which have been previously described for the treatment of stable angina pectoris or erectile dysfunction.

Compounds (5), (6), (7), (8), (9), (10), (11), (12) and (13) are known as sGC activators.

PDE-5 inhibitors which are useful for the combined treatment of urological disorders are in particular Tadalafil ((6R,12aR)-2,3,6,7,12,12a-Hexahydro-2-methyl-6-(3,4-methylene-dioxyphenyl)pyrazino(1',2':1,6)pyrido(3,4-b)indole-1,4-dione), Vardenafil (2-(2-Ethoxy-5-(4-ethylpiperazin-1-yl-1-sulfonyl)phenyl)-5-methyl-7-propyl-3H-imidazo (5,1-f) (1,2,4)triazin-4-one), Sildenafil (3-[2-ethoxy-5-(4-methylpiperazin-1-yl)sulfonyl-phenyl]-7-methyl-9-propyl-2,4,7,8-tetrazabicyclo[4.3.0]nona-3,8,10-trien-5-one), Udenafil 5-[2-propyloxy-5-(1-methyl-2-pyrrolidinylethylamidosulfonyl)phenyl]-methyl-3-propyl-1,6-dihydro-7H-pyrazolo(4,3-d)pyrimidine-7-one, Dasantafil 7-(3-Bromo-4-methoxybenzyl)-1-ethyl-8-[[(1,2)-2-hydroxycyclopentyl]amino]-3-(2-hydroxyethyl)-3,7-dihydro-1-purine-2,6-dione, Avanafil 4-{[(3-chloro-4-methoxyphenyl)methyl]amino}-2-[(2S)-2-(hydroxymethyl)pyrrolidin-1-yl]-N-(pyrimidin-2-ylmethyl)pyrimidine-5-carboxamide, Mirodenafil, Lodenafil, UK 369.003, UK 371.800, SLx 2101 of Surface Logix, LAS 34179Triazolo[1,2-]xanthine, 6-methyl-4-propyl-2-[2-propoxy-5-(4-methylpiperazino) sulfonyl]phenyl-, or salts, hydrates or hydrates of salts of the before mentioned PDE5 inhibitors.

VX-809, VX-770, VX-661 are known and correspond to the formulae shown below:

A pharmaceutical composition of the invention is formulated to be compatible with its intended route of administration. Examples of routes of administration include parenteral e.g., intravenous, intradermal, subcutaneous' oral (e.g. 'inhalation)' transdermal (topical) transmucosal and rectal administration. Pharmaceutical compositions suitable for injectable use include sterile aqueous solutions (where water soluble) or dispersions and sterile powders for the extemporaneous preparation of sterile injectable solutions or dispersions. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents for example, parabens, chlorobutanol, phenol, ascorbic acid, thimerosal, and the like. In many cases, it will be preferable to include isotonic agents, for example, sugars, polyalcohols such as maitol sorbitol sodium chloride in the composition.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or con1 starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g. 'a gas such as carbon dioxide, or a nebulizer.

Systemic administration can also be by transmucosal or transderrnal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Bio degradable, biocompatible polymers can be used, such as ethylene vinyl acetate, polyanhydrides, polyglycolic acid, collagen, polyorthoesters, and polylactic acid.

In another embodiment the invention provides sGC stimulators or sGC activators and/or PDE5 inhbitiors in combination with other pharmacological compounds which lead to increased cGMP mobilization, i.e. Nitrates, NO-Donors, Natriumnitroprussid, Nitro-glycerine, Isosorbidmononitrate, Isosorbiddinitrate, Molsidomin or SIN-1, inhaled Nitric Oxide, which are useful for the treatment of Cystic Fibrosis (CF), and superior in efficacy over methods of treatment already known or compounds correcting and potentiating i.e. deltaF508 CFTR function, i.e. VX-809, VX-770, VX-661 which are useful for the treatment of Cystic Fibrosis (CF), and superior in efficacy over methods of treatment already known or the current standard of care in CF, i.e. systemic or nebulized antibiotics, Dornase Alpha (rhDNase), hypertonic saline, asthma treatments, which are useful for the treatment of Cystic Fibrosis (CF), and superior in efficacy over methods of treatment already known or with anti-inflammatory drugs, i.e. systemic or nebulized glucocorticoids, serine protease inhibitors, elastase inhibitors which are useful for the treatment of Cystic Fibrosis (CF), and superior in efficacy over methods of treatment already known and their use for the preparation of pharmaceutical compositions for Cystic Fibrosis (CF), whereby these combinations comprise either i) pharmaceutical compositions comprising a compound having a sGC stimulatory or activatory action and/or PDE-5 inhibitory activity in combination with other pharmacological compounds which lead to increased cGMP mobilization, i.e. Nitrates, NO-Donors, Natriumnitroprussid, Nitroglycerine, Isosorbidmononitrate, Isosorbiddinitrate, Molsidomin or SIN-1, inhaled Nitric Oxide, which are useful for the treatment of Cystic Fibrosis (CF), and superior in efficacy over methods of treatment already known or compounds correcting and potentiating i.e. deltaF508 CFTR function, i.e. VX-809, VX-770, VX-661 which are useful for the treatment of Cystic Fibrosis (CF), and superior in efficacy over methods of treatment already known or the current standard of care in CF, i.e. systemic or nebulized antibiotics, Dornase Alpha (rhDNase), hypertonic saline, asthma treatments, which are useful for the treatment of Cystic Fibrosis (CF), and superior in efficacy over methods of treatment already known or with anti-inflammatory drugs, i.e. systemic or nebulized glucocorticoids, serine protease inhibitors, elastase inhibitors which are useful for the treatment of Cystic Fibrosis (CF), and superior in efficacy over methods of treatment already known, or ii) pharmaceutical compositions comprising one sGC stimulator and sGC activator and/or at least one PDE-5 inhibitor in combination with other pharmacological compounds which lead to increased cGMP mobilization, i.e. Nitrates, NO-Donors, Natriumnitroprussid, Nitroglycerine, Isosorbidmononitrate, Isosorbiddinitrate, Molsidomin or SIN-1, inhaled Nitric Oxide, which are useful for the treatment of Cystic Fibrosis (CF), and superior in efficacy over methods of treatment already known or compounds correcting and potentiating i.e. deltaF508 CFTR function, i.e. VX-809, VX-770, VX-661 which are useful for the treatment of Cystic Fibrosis (CF), and superior in efficacy over methods of treatment already known or the current standard of care in CF, i.e. systemic or nebulized antibiotics, Dornase Alpha (rhDNase), hypertonic saline, asthma treatments, which are useful for the treatment of Cystic Fibrosis (CF), and superior in efficacy over methods of treatment already known or with anti-inflammatory drugs, i.e. systemic or nebulized glucocorticoids, serine protease inhibitors, elastase inhibitors which are useful for the treatment of Cystic Fibrosis (CF), and superior in efficacy over methods of treatment already known as a fixed combination in one application unit, or iii) a kit of parts containing at least two sets of pharmaceutical compositions, each set consisting of at least one pharmaceutical preparation comprising a PDE-5 inhibitor in units of at least one dose and at least one pharmaceutical preparation comprising a sGC activator or sGC stimulator in units of at least one dose in combination with other pharmacological compounds which lead to increased cGMP mobilization, i.e. Nitrates, NO-Donors, Natriumnitroprussid, Nitroglycerine, Isosorbidmononitrate, Isosorbiddinitrate, Molsidomin or SIN-1, inhaled Nitric Oxide, which are useful for the treatment of Cystic Fibrosis (CF), and superior in efficacy over methods of treatment already known or compounds correcting and potentiating i.e. deltaF508 CFTR function, i.e. VX-809, VX-770, VX-661 which are useful for the treatment of Cystic Fibrosis (CF), and superior in efficacy over methods of treatment already known or the current standard of care in CF, i.e. systemic or nebulized antibiotics, Dornase Alpha (rhDNase), hypertonic saline, asthma treatments, which are useful for the treatment of Cystic Fibrosis (CF), and superior in efficacy over methods of treatment already known or with anti-inflammatory drugs, i.e. systemic or nebulized glucocorticoids, serine protease inhibitors, elastase inhibitors which are useful for the treatment of Cystic Fibrosis (CF), and superior in efficacy over methods of treatment already known, whereby each application unit of said pharmaceutical compositions is administered in combination, sequentially, as single dose or in multiple doses.

In Particular, the Present Invention Provides:

A pharmaceutical composition for the treatment of a disease comprised in a group of diseases consisting of Cystic Fibrosis (CF), containing at least one compound selected from 2-[1-(2-fluorobenzyl)-1H-pyrazolo[3,4-b]pyridine-3-yl]-5-(4-morpholinyl)-4,6-pyrimidinediamine (1), 2-[1-(2-fluorobenzyl)-1H-pyrazolo[3,4-b]pyridine-3-yl]-5-(4-pyridinyl)-4-pyrimidinamine (2),
methyl-4,6-diamino-2-[1-(2-fluorobenzyl)-1H-pyrazolo[3,4-b]pyridine-3-yl]-5-pyrimidinyl-(methyl)carbamate (3),
methyl-{4,6-diamino-2-[5-fluor-1-(2-fluorbenzyl)-1H-pyrazolo[3,4-b]pyridine-3-yl]pyrimidine-5-yl}carbamate (3a),
methyl-4,6-diamino-2-[1-(2-fluorobenzyl)-1H-pyrazolo[3,4-b]pyridine-3-yl]-5-pyrimidinylcarbamate (4),
3-(4-amino-5-cyclopropylpyrimidine-2-yl)-1-(2-fluorbenzyl)1H-pyrazolo[3,4-b]pyridine (4a),
and
5-chloro-2-(5-chlorothiophene-2-sulfonylamino-N-(4-(morpholine-4-sulfonyl)-phenyl)-benzamide sodium salt (6),
2-(4-chloro-phenylsulfonylamino)-4,5-dimethoxy-N-(4-(thiomorpholine-4-sulfonyl)-phenyl)-benzamide (7),
and
4-({(4-carboxybutyl)[2-(2-{[4-(2-phenylethyl)benzyl]oxy}phenyl)ethyl]amino}methyl)benzoic acid (5)
1-{6-[5-chloro-2-({4-trans-4-}trifluoromethyl)cyclohexyl]benzyl}oxy)phenyl]pyridin-2-yl}-5-(trifluoromethyl)-1H-pyrazole-4-carboxylic acid (8)
1-[6-(2-(2-methyl-4-(4-trifluoromethoxyphenyl)benzyloxy)-phenyl)pyridin-2-yl]-5-trifluoromethyl-pyrazole-4-carboxylic acid (9)
1[6-(3,4-dichlorophenyl)-2-pyridinyl-5-(trifluoromethyl)-1H-pyrazole-4-caboxylic acid (10)
1-({2-[3-chloro-5-(trifluoromethyl)phenyl]-5-methyl-1,3-thiazol-4-yl}methyl)-1H-pyrazole-4-carboxylic acid (11)
4-({2-[3-(trifluoromethyl)phenyl]-1,3-thiazol-4-yl}methyl)benzoic acid (12)
1-({2-[2-fluoro-3-(trifluoromethyl)phenyl]-5-methyl-1,3-thiazol-4-yl}methyl)-1H-pyrazole-4-carboxylic acid (13)
and/or
Tadalafil ((6R,12aR)-2,3,6,7,12,12a-Hexahydro-2-methyl-6-(3,4-methylene-dioxyphenyl)pyrazino(1',2':1,6)pyrido(3,4-b)indole-1,4-dione), Vardenafil (2-(2-Ethoxy-5-(4-ethylpiperazin-1-yl-1-sulfonyl)phenyl)-5-methyl-7-propyl-3H-imidazo (5,1-f) (1,2,4)triazin-4-one), Sildenafil (3-[2-ethoxy-5-(4-methylpiperazin-1-yl)sulfonyl-phenyl]-7-methy-I-9-propyl-2,4,7,8-tetrazabicyclo [4.3.0]nona-3,8,10-trien-5-one), Udenafil 5-[2-propyloxy-5-(1-methyl-2-pyrrolidinyl-ethyl-amidosulfonyl)phenyl]-methyl-3-propyl-1,6-dihydro-7H-pyrazolo(4,3-d)pyrimidine-7-one,
Dasantafil 7-(3-Bromo-4-methoxybenzyl)-1-ethyl-8-[[(1,2)-2-hydroxycyclopentyl]amino]-3-(2-hydroxyethyl)-3,7-dihydro-1-purine-2,6-dione, Avanafil 4-{[(3-chloro-4-methoxyphenyl)methyl]amino}-2-[(2S)-2-(hydroxymethyl)pyrrolidin-1-yl]-N-(pyrimidin-2-yl methyl)pyrimidine-5-carboxamide, Mirodenafil, Lodenafil, UK 369.003, UK 371.800, SLx 2101 of Surface Logix, and/or LAS 34179Triazolo[1,2-]xanthine, 6-methyl-4-propyl-2-[2-propoxy-5-(4-methylpiperazino)-sulfonyl]phenyl or salts, hydrates or hydrates of salts of the before mentioned PDE5 inhibitors.

A pharmaceutical composition for the treatment of a disease comprised in a group of diseases in which altered CFTR-function is causally involved, consisting but not limited to pancreatic disorders, gastrointestinal disorders, liver disorders, Cystic Fibrosis-related diabetes (CFRD), dry eye, dry mouth, Sjoegren's syndrome, containing at least one compound selected from
2-[1-(2-fluorobenzyl)-1H-pyrazolo[3,4-b]pyridine-3-yl]-5-(4-morpholinyl)-4,6-pyrimidinediamine (1),
2-[1-(2-fluorobenzyl)-1H-pyrazolo[3,4-b]pyridine-3-yl]-5-(4-pyridinyl)-4-pyrimidinamine (2),
methyl-4,6-diamino-2-[1-(2-fluorobenzyl)-1H-pyrazolo[3,4-b]pyridin-3-yl]-5-pyrimidinyl-(methyl)carbamate (3),
methyl-{4,6-diamino-2-[5-fluor-1-(2-fluorbenzyl)-1H-pyrazolo[3,4-b]pyridine-3-yl]pyrimidine-5-yl}carbamate (3a),
methyl-4,6-diamino-2-[1-(2-fluorobenzyl)-1H-pyrazolo[3,4-b]pyridin-3-yl]-5-pyrimidinylcarbamate (4),
3-(4-amino-5-cyclopropylpyrimidine-2-yl)-1-(2-fluorbenzyl)1H-pyrazolo[3,4-b]pyridine (4a),
and
5-chloro-2-(5-chlorothiophene-2-sulfonylamino-N-(4-(morpholine-4-sulfonyl)-phenyl)-benzamide sodium salt (6),
2-(4-chloro-phenylsulfonylamino)-4,5-dimethoxy-N-(4-(thiomorpholine-4-sulfonyl)-phenyl)-benzamide (7),
and
4-({(4-carboxybutyl)[2-(2-{[4-(2-phenylethyl)benzyl]oxy}phenyl)ethyl]amino}methyl) benzoic acid (5)
1-{6-[5-chloro-2-({4-trans-4-}trifluoromethyl)cyclohexyl]benzyl}oxy)phenyl]pyridin-2-yl}-5-(trifluoromethyl)-1H-pyrazole-4-carboxylic acid (8)
1-[6-(2-(2-methyl-4-(4-trifluoromethoxyphenyl)benzyloxy)-phenyl)pyridin-2-yl]-5-trifluoromethyl-pyrazole-4-carboxylic acid (9)
1[6-(3,4-dichlorophenyl)-2-pyridinyl-5-(trifluoromethyl)-1H-pyrazole-4-caboxylic acid (10)
1-({2-[3-chloro-5-(trifluoromethyl)phenyl]-5-methyl-1,3-thiazol-4-yl}methyl)-1H-pyrazole-4-carboxylic acid (11)
4-({2-[3-(trifluoromethyl)phenyl]-1,3-thiazol-4-yl}methyl)benzoic acid (12)
1-({2-[2-fluoro-3-(trifluoromethyl)phenyl]-5-methyl-1,3-thiazol-4-yl}methyl)-1H-pyrazole-4-carboxylic acid (13)
and at least one compound selected from
Tadalafil ((6R,12aR)-2,3,6,7,12,12a-Hexahydro-2-methyl-6-(3,4-methylene-dioxyphenyl)pyrazino(1',2':1,6)pyrido(3,4-b)indole-1,4-dione), Vardenafil (2-(2-Ethoxy-5-(4-ethylpiperazin-1-yl-1-sulfonyl)phenyl)-5-methyl-7-propyl-3H-imidazo (5,1-f) (1,2,4)triazin-4-one), Sildenafil (3-[2-ethoxy-5-(4-methylpiperazin-1-yl)sulfonyl-phenyl]-7-methy-I-9-propyl-2,4,7,8-tetrazabicyclo [4.3.0]nona-3,8,10-trien-5-one), Udenafil 5-[2-propyloxy-5-(1-methyl-2-pyrrolidinyl-ethyl-amidosulfonyl)phenyl]-methyl-3-propyl-1,6-dihydro-7H-pyrazolo(4,3-d)pyrimidine-7-one,
Dasantafil 7-(3-Bromo-4-methoxybenzyl)-1-ethyl-8-[[(1,2)-2-hydroxycyclopentyl]amino]-3-(2-hydroxyethyl)-3,7-dihydro-1-purine-2,6-dione, Avanafil 4-{[(3-chloro-4-methoxyphenyl)methyl]amino}-2-[(2S)-2-(hydroxymethyl)pyrrolidin-1-yl]-N-(pyrimidin-2-ylmethyl)pyrimidine-5-carboxamide, Mirodenafil, Lodenafil, UK 369.003, UK 371.800, SLx 2101 of Surface Logix, and/or LAS 34179Triazolo[1,2-]xanthine, 6-methyl-4-propyl-2-[2-propoxy-5-(4-methylpiperazino)-sulfonyl]phenyl or salts, hydrates or hydrates of salts of the before mentioned PDE5 inhibitors.

Use of a sGC stimulator and activator for the preparation of a pharmaceutical composition for the treatment of Cystic Fibrosis (CF).

Use of a sGC stimulator and activator for the preparation of a pharmaceutical composition for the treatment of pancreatic disorders, gastronintestinal disorders, liver disorders, Cystic Fibrosis-related diabetes (CFRD), dry eye, dry mouth, Sjoegren's syndrome.

Use of a combination of at least one sGC stimulator or activator and at least one PDE5 inhibitor for the preparation of a pharmaceutical composition for the treatment of Cystic Fibrosis (CF).

Use of a combination of at least one sGC stimulator or activator and at least one PDE5 inhibitor for the preparation of a pharmaceutical composition for the treatment of pancreatic disorders, liver disorders, Cystic Fibrosis-related diabetes (CFRD), dry eye, dry mouth, Sjoegren's syndrome.

Use of sGC stimulator or activator selected from the group of sGC stimulators and activators of 2-[1-(2-fluorobenzyl)-1H-pyrazolo[3,4-b]pyridin-3-yl]-5-(4-morpholinyl)-4,6-pyrimidinediamine(1), 2-[1-(2-fluorobenzyl)-1H-pyrazolo[3,4-b]pyridin-3-yl]-5-(4-pyridinyl)-4-pyrimidinamine (2), methyl-4,6-diamino-2-[1-(2-fluorobenzyl)-1H-pyrazolo[3,4-b]pyridin-3-yl]-5-pyrimidinyl(methyl)carbamate (3), methyl-4,6-diamino-2-[1-(2-fluorobenzyl)-1H-pyrazolo[3,4-b]pyridin-3-yl]-5-pyrimidinylcarbamate (4), 5-chloro-2-(5-chlorothiophene-2-sulfonylamino-N-(4-(morpholine-4-sulfonyl)-phenyl)-benzamide sodium salt (6), 2-(4-chlorophenylsulfonylamino)-4,5-dimethoxy-N-(4-(thiomorpholine-4-sulfonyl)-phenyl)-benzamide (7), 4-({(4-carboxybutyl)[2-(2-{[4-(2-phenylethyl)benzyl]oxy}phenyl)ethyl]amino}methyl)benzoic acid (5), 1-{6-[5-chloro-2-({4-trans-4-}trifluoromethyl)cyclohexyl]benzyl}oxy)phenyl]pyridin-2-yl}-5-(trifluoromethyl)-1H-pyrazole-4-carboxylic acid (8), 1-[6-(2-(2-methyl-4-(4-trifluoromethoxyphenyl)benzyloxy)-phenyl)pyridin-2-yl]-5-trifluoromethyl-pyrazole-4-carboxylic acid (9), 1[6-(3,4-dichlorophenyl)-2-pyridinyl-5-(trifluoromethyl)-1H-pyrazole-4-caboxylic acid (10), 1-({2-[3-chloro-5-(trifluoromethyl)phenyl]-5-methyl-1,3-thiazol-4-yl}methyl)-1H-pyrazole-4-carboxylic acid (11), 4-({2-[3-(trifluoromethyl)phenyl]-1,3-thiazol-4-yl}methyl)benzoic acid (12), 1-({2-[2-fluoro-3-(trifluoromethyl)phenyl]-5-methyl-1,3-thiazol-4-yl}methyl)-1H-pyrazole-4-carboxylic acid (13) for the preparation of a pharmaceutical composition for the treatment of Cystic Fibrosis (CF).

Use of a combination of at least one sGC stimulator and activator selected from the group of sGC stimulators and activators of 2-[1-(2-fluorobenzyl)-1H-pyrazolo[3,4-b]pyridine-3-yl]-5-(4-morpholinyl)-4,6-pyrimidinediamine (1), 2-[1-(2-fluorobenzyl)-1H-pyrazolo[3,4-b]pyridine-3-yl]-5-(4-pyridinyl)-4-pyrimidinamine (2), methyl-4,6-diamino-2-O-(2-fluorobenzyl)-1H-pyrazolo[3,4-b]pyridine-3-yl]-5-pyrimidinyl(methyl)carbamate (3), methyl-4,6-diamino-2-[1-(2-fluorobenzyl)-1H-pyrazolo[3,4-b]pyridin-3-yl]-5-pyrimidinylcarbamate (4), 3-(4-amino-5-cyclopropylpyrimidine-2-yl)-1-(2-fluorbenzyl)1H-pyrazolo[3,4-b]pyridine (4a), 5-chloro-2-(5-chlorothiophene-2-sulfonylamino-N-(4-(morpholine-4-sulfonyl)-phenyl)-benzamide sodium salt (6), 2-(4-chlorophenylsulfonylamino)-4,5-dimethoxy-N-(4-(thiomorpholine-4-sulfonyl)-phenyl)-benzamide (7), and 4-({(4-carboxybutyl)[2-(2-{[4-(2-phenylethyl)benzyl]oxy}phenyl)ethyl]amino}methyl) benzoic acid (5), 1-{6-[5-chloro-2-({4-trans-4-}trifluoromethyl)cyclohexyl]benzyl}oxy)phenyl]pyridin-2-yl}-5-(trifluoromethyl)-1H-pyrazole-4-carboxylic acid (8), 1-[6-(2-(2-methyl-4-(4-trifluoromethoxyphenyl)benzyloxy)-phenyl)pyridin-2-yl]-5-trifluoromethyl-pyrazole-4-carboxylic acid (9), 1[6-(3,4-dichlorophenyl)-2-pyridinyl-5-(trifluoromethyl)-1H-pyrazole-4-caboxylic acid (10), 1({2-[3-chloro-5-(trifluoromethyl)phenyl]-5-methyl-1,3-thiazol-4-yl}methyl)-1H-pyrazole-4-carboxylic acid (11), 4-({2-[3-(trifluoromethyl)phenyl]-1,3-thiazol-4-yl}methyl)benzoic acid (12), 1-({2-[2-fluoro-3-(trifluoromethyl)phenyl]-5-methyl-1,3-thiazol-4-yl}methyl)-1H-pyrazole-4-carboxylic acid (13)

and at least one PDE-5 inhibitor selected from the group of PDE-5 inhibitors consisting of Vardenafil (2-(2-Ethoxy-5-(4-ethylpiperazin-1-yl-1-sulfonyl)phenyl)-5-methyl-7-propyl-3H-imidazo(5,1-f)(1,2,4)triazin-4-one), Sildenafil (3-[2-ethoxy-5-(4-methylpiperazin-1-yl)sulfonyl-phenyl]-7-methy I-9-propy I-2,4,7,8-tetrazabicyclo[4.3.0]nona-3,8,10-trien-5-one), and Tadalafil ((6R,12aR)-2,3,6,7,12,12a-Hexahydro-2-methyl-6-(3,4-methylene-dioxyphenyl) for the preparation of a pharmaceutical composition for the treatment of Cystic Fibrosis (CF).

A method for the preparation of a pharmaceutical composition for the treatment of the diseases as mentioned above wherein stimulator and activator of the soluble guanylate-cyclase is selected from the group of compounds consisting of 2-[1-(2-fluorobenzyl)-1H-pyrazolo[3,4-b]pyridine-3-yl]-5-(4-morpholinyl)-4,6-pyrimidinediamine (1), 2-[1-(2-fluorobenzyl)-1H-pyrazolo[3,4-b]pyridine-3-yl]-5-(4-pyridinyl)-4-pyrimidinamine (2), methyl-4,6-diamino-2-[1-(2-fluorobenzyl)-1H-pyrazolo[3,4-b]pyridine-3-yl]-5-pyrimidinyl-(methyl)carbamate (3), methyl-{4,6-diamino-2-[5-fluor-1-(2-fluorbenzyl)-1H-pyrazolo[3,4-b]pyridine-3-yl]pyrimidine-5-yl}carbamate (3a), methyl-4,6-diamino-2-[1-(2-fluorobenzyl)-1H-pyrazolo[3,4-b]pyridin-3-yl]-5-pyrimidinylcarbamate (4), 3-(4-amino-5-cyclopropylpyrimidine-2-yl)-1-(2-fluorbenzyl)1H-pyrazolo[3,4-b]pyridine (4a), 5-chloro-2-(5-chlorothiophene-2-sulfonylamino-N-(4-(morpholine-4-sulfonyl)-phenyl)-benzamide sodium salt (6), 2-(4-chlorophenylsulfonylamino)-4,5-dimethoxy-N-(4-(thiomorpholine-4-sulfonyl)-phenyl)-benzamide (7), 4-({(4-carboxybutyl)[2-(2-{[4-(2-phenylethyl)benzyl]oxy}phenyl)ethyl]amino}methyl)benzoic acid (5), 1-{6-[5-chloro-2-({4-trans-4-}-trifluoromethyl)cyclohexyl]benzyl}oxy)phenyl]pyridin-2-yl}-5-(trifluoromethyl)-1H-pyrazole-4-carboxylic acid (8), 1-[6-(2-(2-methyl-4-(4-trifluoromethoxyphenyl)benzyloxy)-phenyl)pyridin-2-yl]-5-trifluoromethyl-pyrazole-4-carboxylic acid (9), 1[6-(3,4-dichlorophenyl)-2-pyridinyl-5-(trifluoromethyl)-1H-pyrazole-4-caboxylic acid (10), 1-({2-[3-chloro-5-(trifluoromethyl)phenyl]-5-methyl-1,3-thiazol-4-yl}methyl)-1H-pyrazole-4-carboxylic acid (11), 4-({2-[3-(trifluoromethyl)phenyl]-1,3-thiazol-4-yl}methyl)benzoic acid (12), 1-({2-[2-fluoro-3-(trifluoromethyl)phenyl]-5-methyl-1,3-thiazol-4-yl}methyl)-1H-pyrazole-4-carboxylic acid (13).

Use of a pharmaceutical composition as mentioned above for the stimulation and activation of the soluble guanylate cyclase in a mammal having Cystic Fibrosis (CF).

Use of a pharmaceutical composition as mentioned above for the stimulation and activation of the soluble guanylate cyclase and for the regulation of PDE activity in a mammal having Cystic Fibrosis (CF).

A pharmaceutical composition containing at least methyl-4,6-diamino-2-[1-(2-fluorobenzyl)-1H-pyrazolo[3,4-b]pyridine-3-yl]-5-pyrimidinylcarbamate (4) and/or 4-({(4-carboxybutyl)[2-(2-{[4-(2-phenylethyl) benzyl] oxy}phenyl) ethyl]amino}methyl) benzoic acid (5) and at least Sildenafil, Tadalafil, Udenafil, Dasantafil, Avanafil, Mirodenafil, Lodenafil, UK 369.003, UK 371.800, SLx2101 and LAS34179 and preferably Vardenafil or a salt, a hydrat or a hydrat of a salt of the before mentioned PDE5 inhibitors, for the treatment of Cystic Fibrosis (CF).

In order to clarify the effect of sGC stimulators and sGC activators alone and in combination with vardenafil experiments are performed.

In particular sGC stimulators and sGC activators, i.e. methyl-4,6-diamino-2-[1-(2-fluorobenzyl)-1H-pyrazolo[3,4-b]pyridine-3-yl]-5-pyrimidinylcarbamate (4) alone and in combination with PDE5 inhibitors, i.e. Vardenafil were tested in vitro and in vivo:

in transgenic mice expressing the delta F508CFTR channel, on nasal potential difference, on salivation secretion as on salivation chloride content as descriebed recently (Droebner et al. Journal of Cystic Fibrosis, under review).

in transgenic mice not expressing the CFTR, on nasal potential difference, on salivation secretion as on salivation chloride content. as descriebed recently (Droebner et al. Journal of Cystic Fibrosis, under review).

Combinations of sGC stimulators and activators, i.e. methyl-4,6-diamino-2-[1-(2-fluorobenzyl)-1H-pyrazolo[3,4-b]pyridine-3-yl]-5-pyrimidinylcarbamate (4) with PDE5 inhibitors, i.e. vardenafil are safe, with a hemodynamic profile similar to vardenafil.

The preferred embodiment of the invention is a combination of at least one sGC stimulator or activator selected from the group comprising of 2-[1-(2-fluorobenzyl)-1H-pyrazolo[3,4-b]pyridine-3-yl]-5-(4-morpholinyl)-4,6-pyrimidinediamine (1), 2-[1-(2-fluorobenzyl)-1H-pyrazolo[3,4-b]pyridine-3-yl]-5-(4-pyridinyl)-4-pyrimidinamine (2), methyl-4,6-diamino-2-[1-(2-fluorobenzyl)-1H-pyrazolo[3,4-b]pyridine-3-yl]-5-pyrimidinyl(methyl)carbamate (3), methyl-4,6-diamino-2-[1-(2-fluorobenzyl)-1H-pyrazolo[3,4-b]pyridin-3-yl]-5-pyrimidinylcarbamate (4), 3-(4-amino-5-cyclopropylpyrimidine-2-yl)-1-(2-fluorbenzyl)1H-pyrazolo[3,4-b]pyridine (4a), 5-chloro-2-(5-chlorothiophene-2-sulfonylamino-N-(4-(morpholine-4-sulfonyl)-phenyl)-benzamide sodium salt (6), 2-(4-chlorophenylsulfonylamino)-4,5-dimethoxy-N-(4-(thiomorpholine-4-sulfonyl)-phenyl)-benzamide (7), and/or 4-({(4-carboxybutyl)[2-(2-{[4-(2-phenylethyl)benzyl]oxy}phenyl)ethyl]amino}methyl)benzoic acid (5), 1-{6-[5-chloro-2-({4-trans-4-}trifluoromethyl)cyclohexyl]benzyl}oxy)phenyl]pyridin-2-yl}-5-(trifluoromethyl)-1H-pyrazole-4-carboxylic acid (8), 1-[6-(2-(2-methyl-4-(4-trifluoromethoxyphenyl)benzyloxy)-phenyl)pyridin-2-yl]-5-trifluoromethyl-pyrazole-4-carboxylic acid (9), 1[6-(3,4-dichlorophenyl)-2-pyridinyl-5-(trifluoromethyl)-1H-pyrazole-4-caboxylic acid (10), 1-({2-[3-chloro-5-(trifluoromethyl)phenyl]-5-methyl-1,3-thiazol-4-yl}methyl)-1H-pyrazole-4-carboxylic acid (11), 4-({2-[3-(trifluoromethyl)phenyl]-1,3-thiazol-4-yl}methyl)benzoic acid (12), 1-({2-[2-fluoro-3-(trifluoromethyl)phenyl]-5-methyl-1,3-thiazol-4-yl}methyl)-1H-pyrazole-4-carboxylic acid (13) with a PDE5 inhibitor selected form the group comprising Vardenafil, Sildenafil, Tadalafil, Udenafil, Dasantafil, Avanafil, Mirodenafil, Lodenafil, UK 369.003, UK 371.800, SLx2101 and LAS34179 in which the combination comprises 0.1 to 1 mg of the sGC stiumulator or activator and 2.5 to 20 mg of the PDE5 inhibitor in combination with other pharmacological compounds which lead to increased cGMP mobilization, i.e. Nitrates, NO-Donors, Natriumnitroprussid, Nitro-glycerine, Isosorbidmononitrate, Isosorbiddinitrate, Molsidomin or SIN-1, inhaled Nitric Oxide, which are useful for the treatment of Cystic Fibrosis (CF), and superior in efficacy over methods of treatment already known or compounds correcting and potentiating i.e. deltaF508 CFTR function, i.e. VX-809, VX-770, VX-661 which are useful for the treatment of Cystic Fibrosis (CF), and superior in efficacy over methods of treatment already known or the current standard of care in CF, i.e. systemic or nebulized antibiotics, Dornase Alpha (rhDNase), hypertonic saline, asthma treatments, which are useful for the treatment of Cystic Fibrosis (CF), and superior in efficacy over methods of treatment already known or with anti-inflammatory drugs, i.e. systemic or nebulized glucocorticoids, serine protease inhibitors, elastase inhibitors which are useful for the treatment of Cystic Fibrosis (CF), and superior in efficacy over methods of treatment already known Another preferred embodiment of the invention is a combination as described above in which the sGC stimulator or activator is selected from the group comprising 2-[1-(2-fluorobenzyl)-1H-pyrazolo[3,4-b]pyridine-3-yl]-5-(4-morpholinyl)-4,6-pyrimidinediamine (1), 2-[1-(2-fluorobenzyl)-1H-pyrazolo[3,4-b]pyridine-3-yl]-5-(4-pyridinyl)-4-pyrimidinamine (2), methyl-4,6-diamino-2-[1-(2-fluorobenzyl)-1H-pyrazolo[3,4-b]pyridine-3-yl]-5-pyrimidinyl-(methyl)carbamate (3), methyl-{4,6-diamino-2-[5-fluor-1-(2-fluorbenzyl)-1H-pyrazolo[3,4-b]pyridine-3-yl]pyrimidine-5-yl}carbamate (3a), methyl-4,6-diamino-2-[1-(2-fluorobenzyl)-1H-pyrazolo[3,4-b]pyridine-3-yl]-5-pyrimidinylcarbamate (4), 3-(4-amino-5-cyclopropylpyrimidine-2-yl)-1-(2-fluorbenzyl)1H-pyrazolo[3,4-b]pyridine (4a), 5-chloro-2-(5-chlorothiophene-2-sulfonylamino-N-(4-(morpholine-4-sulfonyl)-phenyl)-benzamide sodium salt (6), 2-(4-chlorophenylsulfonylamino)-4,5-dimethoxy-N-(4-(thiomorpholine-4-sulfonyl)-phenyl)-benzamide (7), and/or 4-({(4-carboxybutyl)[2-(2-{[4-(2-phenylethyl)benzyl]oxy}phenyl)ethyl]amino}methyl)benzoic acid (5), 1-{6-[5-chloro-2-({4-trans-4-}trifluoromethyl)cyclohexyl]benzyl}oxy)phenyl]pyridin-2-yl}-5-(trifluoromethyl)-1H-pyrazole-4-carboxylic acid (8), 1-[6-(2-(2-methyl-4-(4-trifluoromethoxyphenyl)benzyloxy)-phenyl)pyridin-2-yl]-5-trifluoromethyl-pyrazole-4-carboxylic acid (9), 1[6-(3,4-dichlorophenyl)-2-pyridinyl-5-(trifluoromethyl)-1H-pyrazole-4-caboxylic acid (10), 1-({2-[3-chloro-5-(trifluoromethyl)phenyl]-5-methyl-1,3-thiazol-4-yl}methyl)-1H-pyrazole-4-carboxylic acid (11), 4-({2-[3-(trifluoromethyl)phenyl]-1,3-thiazol-4-yl}methyl)benzoic acid (12), 1-({2-[2-fluoro-3-(trifluoromethyl)phenyl]-5-methyl-1,3-thiazol-4-yl}methyl)-1H-pyrazole-4-carboxylic acid (13) with a PDE5 inhibitor selected form the group comprising Vardenafil, Sildenafil, Tadalafil, Udenafil, Dasantafil, Avanafil, Mirodenafil, Lodenafil, UK 369.003, UK 371.800, SLx2101 and LAS34179—and at least one other pharmacological compound selected from the group of Nitrates, NO-Donors, Natriumnitroprussid, Nitro-glycerine, Isosorbidmononitrate, Isosorbiddinitrate, Molsidomin or SIN-1, inhaled Nitric Oxide or VX-809, VX-770, VX-661 or systemic or nebulized antibiotics, Dornase Alpha (rhDNase), hypertonic saline, asthma treatments or systemic or nebulized glucocorticoids, serine protease inhibitors, elastase inhibitors.

Another preferred embodiment of the invention is a combination as described above in which the sGC stimulator is methyl-4,6-diamino-2-[1-(2-fluorobenzyl)-1H-pyrazolo[3,4-b]pyridine-3-yl]-5-pyrimidinyl(methyl)carbamate (3), methyl-{4,6-diamino-2-[5-fluor-1-(2-fluorbenzyl)-1H-pyrazolo[3,4-b]pyridine-3-yl]pyrimidine-5-yl}carbamate (3a) or methyl-4,6-diamino-2-[1-(2-fluorobenzyl)-1H-pyrazolo[3,4-b]pyridine-3-yl]-5-pyrimidinylcarbamate (4).

Another preferred embodiment of the invention is a combination as disclosed above in which the PDE5 inhibitor is Vardenafil or Sildenafil.

Another preferred embodiment of the invention is a combination as disclosed above in which the sGC stimulator is methyl-4,6-diamino-2-[1-(2-fluorobenzyl)-1H-pyrazolo[3,4-b]pyridine-3-yl]-5-pyrimidinyl(methyl)carbamate (3), methyl-{4,6-diamino-2-[5-fluor-1-(2-fluorbenzyl)-1H-pyrazolo[3,4-b]pyridine-3-yl]pyrimidine-5-yl}carbamate (3a) or methyl-4,6-diamino-2-[1-(2-fluorobenzyl)-1H-pyrazolo[3,4-b]pyridine-3-yl]-5-pyrimidinylcarbamate (4) and the PDE5 inhibitor is Vardenafil.

Another preferred embodiment of the invention is a combination according to the embodiments disclosed above for the use as a medicament.

Another preferred embodiment of the invention is the use of a combination as disclosed above for the manufacture fo a medicament for the treatment of Cystic Fibrosis (CF).

Another preferred embodiment of the invention is a pharmaceutical formulation comprising at least one combination as disclosed above.

Another preferred embodiment of the invention is a pharmaceutical formulation comprising at least one combination as disclosed above for the use in Cystic Fibrosis (CF).

REFERENCES

Carlile G W, Robert R, Zhang D (2007): Correctors of protein trafficking defects identified by a novel high-throughput screening assay. Chem Bio Chem 8: 1012-1020

Clarke L L (2008): Phosphodiesterase 5 Inhibitors and Cystic Fibrosis. Am J RRespir Crit Care Med 177: 469-472

Cobb B R, Fan L, Kovacs T E (2003): Adenosine receptors and phosphodiesterase inhibitors stimulate Cl⁻ secretion in Calu-3 cells. Am J Respir Cell Mol Biol 29: 410-418

Dormer R L, Harris C M, Clark Z et al. (2004): Sildenafil (Viagra) corrects ΔF508-CFTR location in nasal epithelia cells from patients with cystic fibrosis. Thorax 60: 55-59

Droebner K and Sandner P (2013): Modification of the salivary secretion assay in F508del mice—The murine equivalent of the human sweat test. J Cyst Fibros. [Epub ahead of print] doi:pii: S1569-1993(13)00077-5. 10.1016/j.jcf.2013.05.001.

Evgenov O V, Pacher P, Schmidt P M et al. (2006) NO-independent stimulators and activators of soluble guanylate cyclase: discovery and therapeutic potential. Nat Rev Drug Discov 5(9): 755-68

Lubamba B, Lecourt H, Lebacq J (2008): Preclinical evidence that sildenafil and vardenafil activate chloride transport in cystic fibrosis. Am J Respir Crit Care Med 177: 506-515

McPherson M A, Pereira M M C, Mills C L et al. (1999): A cyclic nucleotide PDE5 inhibitor corrects defective mucin secretion in submanidbular cells containing antibody directed against the cystic fibrosis transmembrane conductance regulator protein. FEBS Letters 464: 48-52

Robert R, Carlile G W, Pavel C et al. (2008): Structural analog of sildenafil identified as a novel corrector of the F508del-CFTR trafficking defect. Mol Pharmacol 73: 478-489.

Sandner P, Hütter J, Tinel H et al. (2007): PDE5 inhibitors beyond erectile dysfunction. Int J Impot Res 19(6): 533-543

Schmidt H H H W., Hoffmann F, Stasch J P, Editors (2009): cGMP: Generators, Effectors and therapeutic implications. Handbook of Experimental Pharmacology Vol. 191

Stasch J P, Becker E M, Alonso-Alija C et al. (2001): N O-independent regulatory site on soluble guanylate cyclase. Nature 8: 212-215

The invention claimed is:

1. A method of treating cystic fibrosis comprising administering a therapeutically effective amount of
   (a) at least one compound selected from the group consisting of methyl-4,6-diamino-2-[1-(2-fluorobenzyl)-1H-pyrazolo[3,4-b]pyridine-3-yl]-5-pyrimidinyl¬(methyl)carbamate (3), methyl-{4,6-diamino-2-[5-fluor-1-(2-fluorbenzyl)-1H-pyrazolo[3,4-b]pyridine-3-yl]pyrimidine-5-yl}carbamate (3a), methyl-4,6-diamino-2-[1-(2-fluorobenzyl)-1H-pyrazolo[3,4-b]pyridine-3-yl]-5-pyrimidinyl¬carbamate (4), and 3-(4-amino-5-cyclopropylpyrimidine-2-yl)-1-(2-fluorbenzyl) 1H-pyrazolo[3,4-b]pyridine (4a), and
   (b) at least one other pharmacological compound selected from the group consisting of VX-809, VX-770, and VX-661
to a patient in need thereof.

2. The method of treating cystic fibrosis according to claim 1, wherein a therapeutically effective amount of (a) methyl-4,6-diamino-2-[1-(2-fluorobenzyl)-1H-pyrazolo[3,4-b]pyridine-3-yl]-5-pyrimidinyl¬(methyl)carbamate (3) and (b) at least one other pharmacological compound selected from the group consisting of VX-809, VX-770, and VX-661 is administered.

3. The method of claim 1, wherein a therapeutically effective amount of methyl-4,6-diamino-2-[1-(2-fluorobenzyl)-1H-pyrazolo[3,4-b]pyridine-3-yl]-5-pyrimidinyl-(methyl)carbamate (3), VX-809 and VX-770 is administered.

4. The method of treating cystic fibrosis according to claim 1, wherein a therapeutically effective amount of methyl-4,6-diamino-2-[1-(2-fluorobenzyl)-1H-pyrazolo[3,4-b]pyridine-3-yl]-5-pyrimidinyl¬(methyl)carbamate (3), VX-661 and VX-770 is administered.

5. A method of treating cystic fibrosis comprising administering a synergistically effective amount of
   (a) at least one compound selected from the group consisting of methyl-4,6-diamino-2-[1-(2-fluorobenzyl)-1H-pyrazolo[3,4-b]pyridine-3-yl]-5-pyrimidinyl¬(methyl)carbamate (3), methyl-{4,6-diamino-2-[5-fluor-1-(2-fluorbenzyl)-1H-pyrazolo[3,4-b]pyridine-3-yl]pyrimidine-5-yl}carbamate (3a), methyl-4,6-diamino-2-[1-(2-fluorobenzyl)-1H-pyrazolo[3,4-b]pyridine-3-yl]-5-pyrimidinyl¬carbamate (4), and 3-(4-amino-5-cyclopropylpyrimidine-2-yl)-1-(2-fluorbenzyl)1H-pyrazolo[3,4-b]pyridine (4a), and
   (b) at least one other pharmacological compound selected from the group consisting of VX-809, VX-770, and VX-661
to a patient in need thereof.

6. The method of treating cystic fibrosis according to claim 5, wherein a synergistically effective amount of (a) methyl-4,6-diamino-2-[1-(2-fluorobenzyl)-1H-pyrazolo[3,4-b]pyridine-3-yl]-5-pyrimidinyl¬(methyl)carbamate (3) and (b) at least one other pharmacological compound selected from the group consisting of VX-809, VX-770, and VX-661 is administered.

7. The method of claim 5, wherein a synergistically effective amount of methyl-4,6-diamino-2-[1-(2-fluorobenzyl)-1H-pyrazolo[3,4-b]pyridine-3-yl]-5-pyrimidinyl-(methyl)carbamate (3), VX-809 and VX-770 is administered.

8. The method of treating cystic fibrosis according to claim 5, wherein a synergistically effective amount of methyl-4,6-diamino-2-[1-(2-fluorobenzyl)-1H-pyrazolo[3,4-b]pyridine-3-yl]-5-pyrimidinyl¬(methyl)carbamate (3), VX-661 and VX-770 is administered.

* * * * *

UNITED STATES PATENT AND TRADEMARK OFFICE
CERTIFICATE OF CORRECTION

PATENT NO. : 10,265,314 B2
APPLICATION NO. : 14/906305
DATED : April 23, 2019
INVENTOR(S) : Sandner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 242 days.

Signed and Sealed this
Nineteenth Day of May, 2020

Andrei Iancu
*Director of the United States Patent and Trademark Office*